US008115064B2

(12) United States Patent
Juarez et al.

(10) Patent No.: US 8,115,064 B2
(45) Date of Patent: Feb. 14, 2012

(54) WATERMELON LINE WAS146-4197

(75) Inventors: Benito Juarez, Woodland, GA (US); Greg Tolla, Woodland, CA (US); Fred McCuiston, Tifton, GA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 69 days.

(21) Appl. No.: 12/198,727

(22) Filed: Aug. 26, 2008

(65) Prior Publication Data
US 2009/0064368 A1    Mar. 5, 2009

Related U.S. Application Data

(60) Provisional application No. 60/968,877, filed on Aug. 29, 2007.

(51) Int. Cl.
*A01H 5/00* (2006.01)
*A01H 5/10* (2006.01)
*A01H 1/00* (2006.01)
*C12N 15/82* (2006.01)
*C12N 5/04* (2006.01)
*C12Q 1/68* (2006.01)

(52) U.S. Cl. ....... 800/308; 435/410; 435/6.11; 800/260; 800/278

(58) Field of Classification Search .................. 800/308
See application file for complete search history.

(56) References Cited

OTHER PUBLICATIONS

Davis et al (2004, Cucurbit Genet. Coop. Rep. 27:34-40).*
U.S. Application No. 200600019 for Plant Variety Protection for Watermelon (Cucurbitaceae—*Citrullus lanatus* var lanatus) Variety 90-4262, dated Oct. 28, 2005.
Plant Breeder's Rights Variety Application No. 2004/022 for Watermelon Variety Companion, Commonwealth of Australia, Jan. 29, 2004.
U.S. PVP Certificate No. 7600027 for Watermelon Variety Sunshade, Jul. 19, 1976.

* cited by examiner

*Primary Examiner* — Anne Kubelik
(74) *Attorney, Agent, or Firm* — SNR Denton US LLP; Alissa M. Eagle Esq

(57) ABSTRACT

The invention provides seed and plants of the watermelon line designated WAS146-4197. The invention thus relates to the plants, seeds and tissue cultures of watermelon line WAS146-4197, and to methods for producing a watermelon plant produced by crossing a plant of watermelon line WAS146-4197 with itself or with another watermelon plant, such as a plant of another line. The invention further relates to seeds and plants produced by such crossing. The invention further relates to parts of a plant of watermelon line WAS146-4197, including the fruit and gametes of such plants.

29 Claims, No Drawings

WATERMELON LINE WAS146-4197

This application claims the priority of U.S. Provisional Appl. Ser. No. 60/968,877, filed Aug. 29, 2007, the entire disclosure of which is incorporated herein by reference.

BACKGROUND OF THE INVENTION

1. Field of the Invention

The present invention relates to the field of plant breeding and, more specifically, to the development of watermelon line WAS146-4197.

2. Description of Related Art

Watermelon, *Citrullus lanatus* (formerly *Citrullus vulgaris*) is of the family Cucubitaceae. Watermelon produces a fruit known called a pepo, which has a thick rind (exocarp) and fleshy center (mesocarp and endocarp). However, consumers typically consider the watermelon fruit a type of melon because it has a smooth, green and/or yellow exterior rind and a juicy, sweet, usually red to yellow, interior flesh. In the United States, Georgia, Florida, Texas, California and Arizona are among the largest watermelon producing states, but approximately 44 states grow watermelon commercially. Watermelon is typically consumed fresh, and can be used to flavor drinks and/or smoothies. Watermelon is approximately 92% water by weight, which is higher than almost any other fruit, and is low calorie while having high nutritional value. For example, a one-cup serving of watermelon provides approximately 50 calories and 14.6 mg of vitamin C. Watermelon also provides significant amounts of vitamins A, B6, and B1, as well as the minerals potassium and magnesium. Certain watermelon may also be a source of the antioxidant, lycopene.

Watermelons are natural diploids, referred to as 2N (N=11), with chromosomes arranged in pairs. Many plants, including watermelons, can undergo a duplication of their entire set of chromosomes and exist as tetraploids, referred to as 4N (4N=44). Watermelon tetraploids can be produced routinely in the laboratory using cell biology techniques.

A tetraploid (4N) female parent can be crossed with diploid (2N) male parent to produce triploid (3N) seeds (3N=33). A hybrid triploid plant produces watermelon fruit which is seedless. Although triploid plants do not usually produce any viable seed, small, white, rudimentary seeds may develop within the fruit and can be eaten with the fruit, as in the case of parthenocarpic cucumber. The number and size of the white, rudimentary seeds varies with the variety. Occasionally a dark, hard seedcoat or a true seed may be found in a triploid watermelon.

A tetraploid seed parent typically produces only 5 to 10% as many seeds as a typical diploid plant. Commercial seed production of a triploid hybrid cultivar requires a substantial amount of seed for a commercially viable product.

Tetraploid parental lines generally have a uniform or "solid" colored rind, i.e., a rind pattern that is primarily one color as opposed to a rind pattern having striping. Generally, the rind of the fruit from tetraploid parental lines has a light green to a creamy green color. This color is also sometimes referred to as "gray."

Historically, seedless watermelons commercialized in the United States and around the world involved creation of triploid hybrids by crossing tetraploid line having a light green rind with a diploid line having a striped rind. Light green rind color is a recessive trait when crossed with a stripped rind. However, in the creation of triploid watermelons by this method, the hybrid will receive two doses of the light green rind gene and one dose of the gene for stripes. The rind pattern of the triploid hybrid although striped, has a faded pattern that may not be perceived as fresh. One advantage of crossing a (preferably) round light green tetraploid and an elongated striped diploid is that it is easy to visually distinguish the inbred lines from the hybrid. One means to obtain a darker-striped triploid watermelon is to use a striped inbred tetraploid crossed to a striped inbred diploid line. However, a drawback to this method is that it may be challenging to visually discriminate between the inbred tetraploid (seeded) and the triploid hybrid (seedless).

There remains a need for improved diploid watermelon lines with good yield, dark rind coloration, small seeds, and a readily distinguishable appearance which can be used to produce triploid fruit which have traits such as, for example, dark stripes, red flesh, small seeds, and high nutritional value.

SUMMARY OF THE INVENTION

In one aspect, the present invention provides a watermelon plant of the line designated WAS146-4197. Also provided are watermelon plants having all the physiological and morphological characteristics of the watermelon line designated WAS146-4197. Parts of the watermelon plant of the present invention are also provided, for example, including a pollen grain, an ovule, a fruit, and a cell of the plant.

The invention also concerns seed of watermelon line WAS146-4197. The watermelon seed of the invention may be provided as an essentially homogeneous population of watermelon seed of the line designated WAS146-4197. Essentially homogeneous populations of seed are generally free from substantial numbers of other seed. Therefore, seed of line WAS146-4197 may be defined as forming at least about 97% of the total seed, including at least about 98%, 99% or more of the seed. The population of watermelon seed may be particularly defined as being essentially free from hybrid seed. The seed population may be separately grown to provide an essentially homogeneous population of watermelon plants designated WAS146-4197.

In another aspect of the invention, a plant of watermelon line WAS146-4197 comprising an added heritable trait is provided. The heritable trait may comprise a genetic locus that is, for example, a dominant or recessive allele. In one embodiment of the invention, a plant of watermelon line WAS146-4197 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line WAS146-4197 is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line WAS146-4197 include those traits set forth in the tables herein, and include for example, yield, maturity, and fruit quality. The regenerable cells in such tissue cultures may be derived from embryos, meristems, cotyledons, pollen, leaves, anthers, roots, root tips, pistil, flower, seed and stalks. Still further, the present invention provides watermelon plants regenerated from a tissue culture of the invention, the plants having all the physiological and morphological characteristics of line WAS146-4197.

In yet another aspect of the invention, processes are provided for producing watermelon seeds, plants and fruit, which processes generally comprise crossing a first parent watermelon plant with a second parent watermelon plant, wherein at least one of the first or second parent watermelon plants is a plant of the line designated WAS146-4197. These processes may be further exemplified as processes for preparing hybrid watermelon seed or plants, wherein a first watermelon plant is crossed with a second watermelon plant of a different, distinct line to provide a hybrid that has, as one of its parents, the watermelon plant line WAS146-4197. In these processes, crossing will result in the production of seed. The seed production occurs regardless of whether the seed is collected or not.

In one embodiment of the invention, the first step in "crossing" comprises planting seeds of a first and second parent watermelon plant, often proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent watermelon plants into plants that bear flowers. A third step may comprise preventing self-pollination of the plants, such as by emasculating the male portions of flowers, (i.e., treating or manipulating the flowers to produce an emasculated parent watermelon plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent watermelon plants. Yet another step comprises harvesting the seeds or from at least one of the parent watermelon plants. The harvested seed can be grown to produce a watermelon plant or hybrid watermelon plant.

The present invention also provides the watermelon seeds and plants produced by a process that comprises crossing a first parent watermelon plant with a second parent watermelon plant, wherein at least one of the first or second parent watermelon plants is a plant of the line designated WAS146-4197. In one embodiment of the invention, watermelon seed and plants produced by the process are first generation ($F_1$) hybrid watermelon seed and plants produced by crossing a plant in accordance with the invention with another, distinct plant. The present invention further contemplates plant parts of such an $F_1$ hybrid watermelon plant, and methods of use thereof. Therefore, certain exemplary embodiments of the invention provide an $F_1$ hybrid watermelon plant and seed thereof.

In still yet another aspect of the invention, the genetic complement of the watermelon plant line designated WAS146-4197 is provided. The phrase "genetic complement" is used to refer to the aggregate of nucleotide sequences, the expression of which sequences defines the phenotype of, in the present case, a watermelon plant, or a cell or tissue of that plant. A genetic complement thus represents the genetic makeup of a cell, tissue or plant, and a hybrid genetic complement represents the genetic make up of a hybrid cell, tissue or plant. The invention thus provides watermelon plant cells that have a genetic complement in accordance with the watermelon plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line WAS146-4197 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by watermelon plant cells, tissues, plants, and seeds, formed by the combination of a haploid genetic complement of a watermelon plant of the invention with a haploid genetic complement of a second watermelon plant, preferably, another, distinct watermelon plant. In another aspect, the present invention provides a watermelon plant regenerated from a tissue culture that comprises a hybrid genetic complement of this invention.

In still yet another aspect, the present invention provides a method of producing a watermelon plant derived from the watermelon line WAS146-4197, the method comprising the steps of: (a) preparing a progeny plant derived from watermelon line WAS146-4197, wherein said preparing comprises crossing a plant of the watermelon line WAS146-4197 with a second watermelon plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating steps (b) and (c) for an additional 3-10 generations to produce a watermelon plant derived from watermelon line WAS146-4197. The plant derived from watermelon line WAS146-4197 may be an inbred line, and step (d) may be defined as comprising sufficient inbreeding to produce the inbred line. In the method, it may be desirable to select particular plants resulting from step (c) for continued crossing according to steps (b) and (c). By selecting plants having one or more desirable traits, a watermelon plant derived from the watermelon line WAS146-4197 is obtained which possesses some of the desirable traits of watermelon line WAS146-4197 as well potentially other selected traits.

In certain embodiments, the present invention provides a method of producing watermelon comprising: (a) cultivating a plant of watermelon line WAS146-4197 to maturity and (b) obtaining at least a first watermelon from the plant.

These and other features and advantages of this invention are described in, or are apparent from, the following detailed description of various exemplary embodiments of the devices and methods according to this invention.

DETAILED DESCRIPTION OF THE INVENTION

The instant invention provides methods and compositions relating to plants, seeds and derivatives of watermelon line WAS146-4197. Watermelon line WAS146-4197 is a diploid inbred line having a plant with non-lobed leaves and the ability to set two or more fruit per plant. The fruit is large with a blocky shape. The non-lobed leaf trait is beneficial during production because it is easy to visually distinguish the female parent plant (usually having lobed leaves) and the male (having non-lobed leaf). Line WAS146-4197 has a rind striping pattern called "very dark mottle stripes" or VDMS, which is a very desirable trait Certain species of fruits and vegetables with a dark exterior, or dark green varieties within a species, are often perceived by consumer as fresher compared to paler species or varieties. The flesh color is a deep red, which is often perceived as desirable to the consumer, and has an average lycopene content of from about 41 to about 49 ppm, including in specific embodiments about 42, 43, 44, 45, 46, 47 and/or about 48 ppm. Typical commercial watermelon hybrids have medium to large seed traces or pips. Certain varieties have small seed traces, but also have a higher probability of having hard seed coats in the fruit. There appears to be a correlation between having tetraploid inbred lines with small seeds and those tetraploids producing triploid with a high occurrence of hard seed coats, when the tetraploid is crossed with a diploid. Line WAS146-4197 has a small seed size, with a seed count of about 30-34 seeds per gram, and this small seed size is dominant to other larger sizes. Therefore, when line WAS146-4197 is the diploid parent in a diploid× tetraploid cross, it produces small seed traces or pips in the triploid hybrids.

Line WAS146-4197 may be useful for producing fruit which has unique and desirable physiological and morphological characteristics. Particularly, this diploid line is useful for crossing with a tetraploid watermelon parent to produce triploid watermelon. Line WAS146-4197 can be used to obtain fruit which has green striping and improved seed yield of both diploid and triploid seeds. This inbred line may be used, for example, to create novel triploid watermelon hybrids with a darker rind.

A. Origin and Breeding History of Diploid Line WAS146-4197

The inbred diploid line was entered in Foundation Seed with the designation of WAS146-4197. The parents of WAS146-4197 are inbred line WAS45-2048S ("204"), WAS110-6433 ("6433"), and WAS110-6315 ("6315"). Line 204 has lobed leaves, medium to medium-small fruit size, very dark mottle stripes, medium seed size, about 17-20 seeds per gram, and dark red flesh color. The second parent, line 6433, having non-lobed leaves, medium to medium-large fruit size and usually two fruit per plant, medium to dark green stripes, and small seeds. The third parent, line 6315, which also has non-lobed leaves, bigger fruit size, medium to dark green stripes, blocky shape, and small seeds.

The first six breeding cycles on this project were carried out in Salama, Guatemala. The cycles are as follows. First, the winter cycle starts in January wherein selections are made and germplasm harvested in April. The second cycle is the summer cycle that begins in May, and selections are made in early August. The third cycle is the fall cycle, and it starts in late August. The selections and germplasm harvest are made in late November.

In the winter cycle of 2001, 204 was crossed to 6433. The F1 hybrid of these two lines was crossed in the spring of 2001 to line 6315. In the fall of 2001, the process of self pollination and selection began. The population appeared to be segregating for the following traits: lobed versus non-lobed leaves, the ability to set fruit, dark versus very dark striping pattern, seed size and color, flesh firmness and color, and fruit shape. Beginning in the fall cycle of 2001, five cycles of self pollination and selection were performed in Guatemala. In the spring cycle of 2004, the populations were grown in Felda, Fla. Several lines were self pollinated, and selection was made for plants with multiple fruit setting ability, large fruit size, lobed and non-lobed leaves, small seed size, very dark mottle stripes (VDMS) striping pattern and darker flesh color with improvements in the firmness level, particularly as compared to 204 and 6433. The selections were then grown and self pollinated in Woodland, Calif. in the summer of 2005. The line was then entered into Foundation Seed. The breeding history can be summarized as follows:

Winter 2001: $F_1$ (204×6433). Spring 2001: $BC_1F_1$ [(204×6433)×6315]. Fall 2001: $BC_1F_2$. Winter 2002: $BC_1F_3$. Spring 2002: $BC_1F_4$. Fall 2002: $BC_1F_5$. Winter 2003: $BC_1F_6$. Spring 2004: $BC_1F_7$. Summer 2005: $BC_1F_8$. The watermelon line WAS146-4197 is particularly adapted to the breeding locations in which it was bred, but is adapted to all watermelon production areas world wide.

B. Physiological and Morphological Characteristics of Watermelon Line WAS146-4197

In accordance with one aspect of the present invention, there is provided a plant having the physiological and morphological characteristics of watermelon line WAS146-4197. The diploid line WAS146-4197 produces fruit which is "blocky" in shape and large in size. The fruit also has a very dark mottled stripes, deep red flash, high lycopene content, and small seeds. A description of the physiological and morphological characteristics of watermelon line WAS146-4197 is presented in Table 1.

TABLE 1

Physiological and Morphological Characteristics of Line WAS146-4197

| 1. CHARACTERISTIC | |
| --- | --- |
| Type | Oblong |
| Area of Best Adaptation | Most Areas |
| Emergence to Anthesis | 5 Days Earlier Than - Charleston Grey |
| Pollination to Maturity | 5 Days Earlier Than - Charleston Grey |
| Ploidy | Diploid |
| 2. Plant | |
| Cotyledon | Flat and Monoecious |
| No. of Flowers per Plant at First Fruit Set | |
| Staminate | 50 |
| Pistillate | 3 |
| No. of Main Stems at Crown | 3 |
| 3. Stem | |
| Shape | Round |
| Diameter at Second Node | 8 mm |
| Pubescent | |
| Vine Length + No. of Internodes (At Last Harvest) | 10 cm |
| 4. Leaf | |
| Shape | Ovate |
| Diameter at Second Node | 8 mm |
| Dorsal Surface | Pubescent |
| Ventral Surface | Smooth |
| Color | Light Green |
| 5. Flower | |
| Stamine | 4 cm Across |
| Perfect | 3 cm Across |
| Color | Yellow |
| 6. Mature Fruit | |
| Shape | Cylindrical |
| Length | 36 cm |
| Diameter at Midsection | 22 cm |
| Index = Length + Diameter × 10 | 16 |
| Average Weight | 7 kg |
| Texture | Smooth |
| Color | Stripe |
| Primary Color | Light Green (Charleston Grey) |
| Secondary Color | Dark Green (Florida Giant) |
| 7. Rind | |
| Texture | Tender |
| Thickness at Blossom End | 7 mm |

TABLE 1-continued

Physiological and Morphological Characteristics of Line WAS146-4197

| | |
|---|---|
| Thickness at Sides | 13 mm |
| 8. Flesh | |
| Crisp | |
| Fine-Little Fiber | |
| Color | |
| Refractomater % Soluble Solids of Juice | 9.4% |
| 9. Seed | |
| Length | 8 mm |
| Width | 5 mm |
| Thickness | 2 mm |
| Index + Length + Width × 10 | 16 |
| Per 1000 Seeds | 27 gm |
| No. Seeds Per Fruit | 900 |
| Color | Dark Brown |

*These are typical values. Values may vary due to environment. Other values that are substantially equivalent are within the scope of the invention.

Line WAS146-4197 produces fruit which are uniform and stable within the limits of environmental influence for all of the traits as described herein. Line WAS146-4197 has been self-pollinated and planted for a number of generations to produce the homozygosity and phenotypic stability to make this line useful in commercial hybrid seed production. No variant traits have been observed or are expected for this line.

Diploid line WAS146-4197 provides sufficient seed yield. Diploid watermelon line WAS146-4197, being substantially homozygous, can be reproduced by planting seeds of the line, growing the resulting watermelon plant under self-pollinating or sib-pollinating conditions and harvesting the resulting seeds using techniques familiar to one of skill in the art.

C. Breeding Watermelon Line WAS146-4197

One aspect of the current invention concerns methods for crossing the watermelon line WAS146-4197 with itself or a second plant and the seeds and plants produced by such methods. These methods can be used for propagation of line WAS146-4197, or can be used to produce hybrid watermelon seeds and the plants grown therefrom. Hybrid seeds are produced by crossing line WAS146-4197 with another watermelon parent line. The watermelon seeds can be used by farmers in the commercial production of watermelons.

Triploid watermelon seeds and plants produced from an inbred diploid watermelon parent WAS146-4197 comprise three sets of alleles, one sets of alleles are the same as line WAS146-4197, with two additional set of alleles derived from the tetraploid watermelon parent line.

The line of the present invention can be used for the development of new triploids based on the elite nature of the genetic background of the line. In selecting a second plant to cross with WAS146-4197 for the purpose of developing novel watermelon varieties, it will typically be preferred to choose those plants which either themselves exhibit one or more selected desirable characteristics or which exhibit the desired characteristic(s) when in hybrid combination. Examples of desirable characteristics include seed yield, germination, fruit size, fruit shape, rind coloring/striping, color of fruit flesh, seedling vigor, maturity, fruit yield, ease of fruit setting, disease tolerance and adaptability for soil and climate conditions.

An analysis was carried out of the performance characteristics of WAS146-4197, including Brix and lycopene content. The results are presented in Tables 2-4 below.

TABLE 2

Performance Characteristics For Line WAS146-4197 (Summer 2007).

| Genotype Units | Harvest Date | Brix % | Lycopene ppm |
|---|---|---|---|
| WAS 146-4197 | July | 8.63 | 45.8 |
| WAS 146-4197 | August | 9.17 | 49.1 |
| WAS 146-4197 | August | 7.88 | 48.4 |
| WAS 146-4197 | August | 8.26 | 47.9 |
| WAS 146-4197 | August | 9.32 | 47.4 |
| WAS 146-4197 | August | 8.34 | 46.6 |
| WAS 146-4197 | August | 9.51 | 45.2 |
| WAS 146-4197 | August | 8.24 | 43.8 |
| WAS 146-4197 | August | 8.15 | 41.6 |
| WAS 146-4197 | August | 8.92 | 41.4 |
| WAS 146-4197 | August | 11.17 | 41.1 |
| WAS 45-2438 (control) | August | 11.68 | 62.4 |

TABLE 3

Analysis of Fruit and Other Characteristics of Line WAS146-4197

| Genotype Units | Rind | Length Cm | Width cm | Rind Thickness cm | Fr Weight lbs. | Flower Col. | Flesh Firmness lb.f | Brix % | Leaf |
|---|---|---|---|---|---|---|---|---|---|
| WAS 146-4197 | VDMS | 35.6 | 20.3 | 1.3 | 17 | Red | 3 | 9.4 | Non-lobed |
| WAS 146-4197 | VDMS | 35.6 | 21.3 | 1.3 | 19 | Red | 3.6 | 8.8 | Non-lobed |
| WAS 146-4197 | VDMS | 36.8 | 22.9 | 1.5 | 22 | Red | 3 | 9.7 | Non-lobed |
| WAS 146-4197 | VDMS | 38.1 | 22.2 | 1.5 | 22.5 | Red | 3.1 | 9.6 | Non-lobed |
| WAS 146-4197 | VDMS | 37.5 | 22.2 | 1.3 | 22 | Red | 4 | 8.6 | Non-lobed |
| WAS 146-4197 | VDMS | 36.1 | 20.6 | 1.5 | 18 | Red | 3 | 9.2 | Non-lobed |
| WAS 146-4197 | VDMS | 35.1 | 21.0 | 1.0 | 17.5 | Red | 3.1 | 9.5 | Non-lobed |
| WAS 146-4197 | VDMS | 35.6 | 21.6 | 1.0 | 20 | Red | 3.6 | 8.7 | Non-lobed |
| WAS 146-4197 | VDMS | 36.1 | 22.6 | 1.3 | 21 | Red | 2.5 | 9.2 | Non-lobed |
| WAS 146-4197 | VDMS | 35.1 | 20.8 | 1.3 | 18 | Red | 3.5 | 8.7 | Non-lobed |
| WAS 146- | VDMS | 35.6 | 20.6 | 1.4 | 17 | Red | 4.4 | 8.3 | Non- |

TABLE 3-continued

Analysis of Fruit and Other Characteristics of Line WAS146-4197

| Genotype Units | Rind | Length Cm | Width cm | Rind Thickness cm | Fr Weight lbs. | Flower Col. | Flesh Firmness lb.f | Brix % | Leaf |
|---|---|---|---|---|---|---|---|---|---|
| 4197 | | | | | | | | | lobed |
| WAS 146-4197 | VDMS | 33.3 | 23.1 | 1.7 | 19.5 | Red | 3.2 | 8.4 | Non-lobed |
| WAS 146-4197 | VDMS | 38.1 | 20.8 | 1.3 | 20 | Red | 3.5 | 9.1 | Non-lobed |
| WAS 146-4730 | VDMS | 36.2 | 21.0 | 1.7 | 19 | Red | 2 | 9.5 | Lobed |
| WAS 146-4730 | VDMS | 38.1 | 21.6 | 1.7 | 22 | Red | 2 | 9 | Lobed |
| WAS 45-2438 | VDMS | 32.4 | 18.4 | 1.9 | 13.5 | Red | 1.5 | 9 | Lobed |
| WAS110-6315 | DMS | 34.3 | 21.0 | 1.3 | 19 | Red | 2.8 | 10.5 | Non-lobed |
| WAS110-6315 | DMS | 33.0 | 21.6 | 1.3 | 17 | Red | 3.4 | 9.4 | Non-lobed |
| WAS110-6315 | DMS | 34.3 | 21.6 | 1.3 | 19.5 | Red | 4 | 8.9 | Non-lobed |
| WAS110-6315 | DMS | 34.3 | 20.3 | 1.3 | 17 | Red | 3.4 | 9.5 | Non-lobed |
| WAS110-6315 | DMS | 34.3 | 20.3 | 1.3 | 18 | Red | 4 | 9 | Non-lobed |
| WAS110-6315 | DMS | 34.9 | 21.6 | 1.3 | 19 | Red | 3.7 | 9.3 | Non-lobed |

TABLE 5

Additional Analysis of Performance Characteristics of Line WAS146-4197 (Summer 2006).

| Variety Units | FruitWt grams | Brix % | Lycopene ppm |
|---|---|---|---|
| WAS146-4197 | 8,907.40 | 9.45 | 76.6 |
| WAS146-4197 | 8,357.50 | 9.19 | 76.8 |
| WAS146-4197 | 8,272.40 | 10.62 | 85.3 |
| WAS45-2438 | 5,645.90 | 9.81 | 70.8 |
| WAS45-2438 | 6,602.80 | 10.09 | 60.0 |
| WAS45-2438 | 7,037.50 | 10.21 | 73.0 |

Watermelon line WAS146-4197 can be crossed with a different variety to produce first generation (F$_1$) watermelon progeny. The hybrid progeny are produced regardless of characteristics of the two varieties produced. As such, an F$_1$ hybrid watermelon plant may be produced by crossing WAS146-4197 with any second watermelon plant. The second watermelon plant may be genetically homogeneous (e.g., inbred) or may itself be a hybrid. Therefore, any F$_1$ hybrid watermelon plant produced by crossing watermelon line WAS146-4197 with a second watermelon plant is a part of the present invention.

The diploid line WAS146-4197 can also be used in the commercial production of triploid watermelon seed. In the production of triploid seed, the diploid and tetraploid parental lines are planted in the same field. Cross-pollination between the tetraploid line, the female parental line of the triploid hybrid seed, and the diploid line, the male parental line, can be accomplished by either natural or mechanical techniques. Natural pollination occurs in watermelon either by self pollination or natural cross pollination, which typically is aided by pollinating organisms. In either natural or artificial crosses, flowering and flowering time are important considerations. Triploid watermelon seeds are produced only in watermelons of diploid plants that are fertilized with pollen of diploid plants. Diploid line WAS146-4197 can be used in combination with any of the known diploid lines to produce triploid watermelon.

The unique traits of WAS146-4197 make it useful as a parental line in the development of new diploid inbreds. Line WAS146-4197 can be used as either a female or male parent to cross with another inbred or hybrid diploid watermelon plant to develop new diploid inbreds. In one embodiment, a WAS146-4197 plant is crossed with another diploid watermelon plant and progeny seed is collected and grown. Further crosses can then be made as determined by a breeder of skill in the art. Progeny plants comprise certain alleles of WAS146-4197, as described above.

When the term watermelon line WAS146-4197 is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those watermelon plants which are developed by a plant breeding technique called backcrossing, wherein essentially all of the desired morphological and physiological characteristics of a variety are recovered in addition to the single locus transferred into the variety via the backcrossing technique. Backcrossing methods can be used with the present invention to improve or introduce a characteristic into the present variety. The parental watermelon plant which contributes the locus for the desired characteristic is termed the nonrecurrent or donor parent. This terminology refers to the fact that the nonrecurrent parent is used one time in the backcross protocol and therefore does not recur. The parental watermelon plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny diploid watermelon plants of a backcross in which WAS146-4197 is the recurrent parent comprise (i) the desired trait from the non-recurrent parent and (ii) all of the physiological and morphological characteristics of diploid watermelon line WAS146-4197 as determined at the 5% significance level when grown in the same environmental conditions.

Watermelon varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, enhanced nutritional quality, yield stability, and yield enhancement. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of watermelon plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of watermelon are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

D. Plants Derived From Watermelon Line WAS146-4197 by Genetic Engineering

Many useful traits that can be introduced by backcrossing, as well as directly into a plant, are those which are introduced by genetic transformation techniques. Genetic transformation may therefore be used to insert a selected transgene into the watermelon line of the invention or may, alternatively, be used for the preparation of transgenes which can be introduced by backcrossing. Methods for the transformation of plants, including watermelon, are well known to those of skill in the art. Techniques which may be employed for the genetic transformation of watermelon include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. Microprojectile bombardment techniques are widely applicable, and may be used to transform virtually any plant species. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target watermelon cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of watermelon plants and expression of foreign genetic elements is exemplified in Choi et al., Genetic transformation and plant regeneration of watermelon using *Agrobacterium tumefaciens*, Plant Cell Rep 13: 344-348 (1994), and Ellul et al., The expression of the *Saccharomyces cerevisiae* HAL1 gene increases salt tolerance in transgenic watermelon [*Citrullus lanatus* (Thunb.) Matsun. & Nakai.], Theor Appl Genet 107: 462-469 (2003).

A number of promoters have utility for plant gene expression for any gene of interest including but not limited to selectable markers, scoreable markers, genes for pest tolerance, disease tolerance, nutritional enhancements and any other gene of agronomic interest. Examples of constitutive promoters useful for watermelon plant gene expression include, but are not limited to, the cauliflower mosaic virus (CaMV) P-35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); a tandemly duplicated version of the CaMV 35S promoter, the enhanced 35S promoter (P-e35S) the nopaline synthase promoter (An et al., Plant Physiol. 88:547, 1988), the octopine synthase promoter (Fromm et al., Plant Cell 1:977, 1989); and the figwort mosaic virus (P-FMV) promoter as described in U.S. Pat. No. 5,378, 619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell 1:961, 1989); or (5) chemicals such as methyl jasmonate, salicylic acid, or Safener. It may also be advantageous to employ organ-specific promoters (e.g., Roshal et al., EMBO J. 6:1155, 1987; Schernthaner et al., EMBO J. 7:1249, 1988; Bustos et al., Plant Cell 1:839, 1989).

Exemplary nucleic acids which may be introduced to the watermelon lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a watermelon plant according to the invention. Non-limiting examples of particular genes and corresponding phenotypes one may choose to introduce into a watermelon plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463, 175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9:207, 1991). The RNA could also be a catalytic RNA molecule (i.e., a ribozyme) engineered to cleave a desired endogenous mRNA product (see for example, Gibson and Shillito, Mol. Biotech. 7:125, 1997). Thus, any gene which produces a protein or mRNA which expresses a phenotype or morphology change of interest is useful for the practice of the present invention.

DEFINITIONS

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Maturity Date: Fruit is considered mature when it has a brix reading of between approximately 8 and 10.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a watermelon variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a watermelon plant by transformation.

Triploid: A cell or organism having three sets of chromosomes.

Deposit Information

A deposit of watermelon line WAS146-4197, disclosed above and recited in the claims, has been made with the American Type Culture Collection (ATCC), 10801 University Blvd., Manassas, Va. 20110-2209. The date of deposit was Jul. 30, 2007. Upon issuance of a patent, all restrictions upon the deposit will be removed, and the deposit is intended to meet all of the requirements of 37 C.F.R. §1.801-1.809. The accession number for those deposited seeds of watermelon line WAS146-4197 is ATCC Accession No. PTA-8559. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997.
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.

Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 18:6531-6535, 1990.
WO 99/31248

What is claimed is:

1. A seed of watermelon line WAS146-4197, a sample of the seed of which has been deposited under ATCC Accession Number PTA-8559.

2. A plant of watermelon line WAS146-4197, a sample of the seed of which has been deposited under ATCC Accession Number PTA-8559.

3. A plant part of the plant of claim 2.

4. The plant part of claim 3, wherein said part is selected from the group consisting of a fruit, a pollen grain, an ovule and a cell.

5. A watermelon plant, or a part thereof, having all the physiological and morphological characteristics of the watermelon plant of claim 2.

6. A tissue culture of regenerable cells of watermelon line WAS146-4197, a sample of the seed of which has been deposited under ATCC Accession Number PTA-8559.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A watermelon plant regenerated from the tissue culture of claim 6, wherein the regenerated plant expresses all of the physiological and morphological characteristics of watermelon line WAS146-4197, a sample of the seed of which has been deposited under ATCC Accession Number PTA-8559.

9. A method of producing watermelon seed, said method comprising crossing a plant of watermelon line WAS146-4197 with a second watermelon plant, wherein a sample of the seed of watermelon line WAS146-4197 has been deposited under ATCC Accession Number PTA-8559.

10. The method of claim 9, wherein said second watermelon plant is tetraploid.

11. The method of claim 9, wherein said second watermelon plant is diploid.

12. The method of claim 9, wherein the plant of watermelon line WAS146-4197 is the male parent.

13. A F1 hybrid seed produced by the method of claim 9.

14. A F1 hybrid plant produced by growing the seed of claim 13.

15. A method for producing a seed of a line WAS146-4197-derived watermelon plant, said method comprising the steps of:
(a) crossing a watermelon plant of line WAS146-4197 with a second watermelon plant, wherein a sample of the seed of watermelon line WAS146-4197 has been deposited under ATCC Accession Number PTA-8559; and
(b) allowing seed of a WAS146-4197-derived watermelon plant to form.

16. The method of claim 15, further comprising the steps of:
(c) crossing a plant grown from said WAS146-4197-derived watermelon seed with itself or a second watermelon plant to yield additional WAS146-4197-derived watermelon seed;
(d) growing said additional WAS146-4197-derived watermelon seed of step
(e) to yield additional WAS146-4197-derived watermelon plants; and
(e) repeating the crossing and growing steps of (c) and (d) to generate further WAS146-4197-derived watermelon plants.

17. A method of producing a watermelon plant derived from line WAS146-4197, said method comprising the steps of:
(a) doubling the chromosome number of a watermelon plant of line WAS146-4197 to produce a tetraploid plant, wherein a sample of the seed of watermelon line WAS146-4197 has been deposited under ATCC Accession Number PTA-8559;
(b) allowing said tetraploid watermelon plant to self-pollinate; and
(c) harvesting seed from said tetraploid watermelon plant.

18. The method of claim 17, further comprising the step of:
(d) crossing said tetraploid watermelon plant with itself or another tetraploid watermelon plant to yield additional WAS146-4197-derived tetraploid watermelon seed;
(e) growing said tetraploid WAS146-4197-derived watermelon seed of step
(d) to yield additional WAS146-4197-derived watermelon plants; and
(f) repeating the crossing and growing steps of (d) and (e) to generate further WAS146-4197-derived tetraploid watermelon plants.

19. The method of claim 17, further comprising growing a diploid reversion of the plant of produced by growing the seed of step (c).

20. A method of vegetatively propagating a plant of watermelon line WAS 146-4197, said method comprising the steps of:
(a) collecting shoot tissue of a watermelon plant according to claim 2;
(b) cultivating said tissue to obtain proliferated shoots; and
(c) rooting said proliferated shoots to obtain rooted plantlets.

21. The method of claim 20, further comprising growing plants from said rooted plantlets.

22. A method of introducing a desired trait into diploid watermelon line WAS146-4197, said method comprising:
(a) crossing a plant of line WAS146-4197, a sample of the seed of which has been deposited under ATCC Accession Number PTA-8559, with a second watermelon plant that comprises a desired trait to produce F1 progeny;
(b) selecting an F1 progeny that comprises the desired trait;
(c) crossing the selected F1 progeny with a plant of line WAS146-4197 to produce backcross progeny;
(d) selecting backcross progeny comprising the desired trait and the physiological and morphological characteristic of watermelon line WAS146-4197; and
(e) repeating steps (c) and (d) three or more times in succession to produce selected fourth or higher backcross progeny that comprise the desired trait and all of the physiological and morphological characteristics of diploid watermelon line WAS146-4197 when grown in the same environmental conditions.

23. A watermelon plant produced by the method of claim 22.

24. A method of producing a plant of watermelon line WAS146-4197 comprising an added desired trait, the method comprising introducing a transgene conferring the desired trait into a plant of watermelon line WAS146-4197, wherein a sample of the seed of watermelon line WAS146-4197 has been deposited under ATCC Accession Number PTA-8559.

25. A plant that comprises all of the physiological and morphological characteristics of watermelon line WAS146-

4197, a sample of the seed of which has been deposited under ATCC Accession Number PTA-8559.

26. A seed that produces the plant of claim 25.

27. A method of determining the genotype of a plant of watermelon line WAS146-4197, a sample of the seed of which has been deposited under ATCC Accession Number PTA-8559, said method comprising detecting in the genome of the plant a plurality of polymorphisms.

28. The method of claim 27, further comprising the step of storing the results of the step of detecting the plurality of polymorphisms on a computer readable medium.

29. A method of producing watermelon, said method comprising:
   (a) cultivating the plant of claim 2 to maturity, and
   (b) obtaining at least a first watermelon from the plant.

* * * * *